United States Patent
Baarman et al.

(10) Patent No.: US 10,401,315 B2
(45) Date of Patent: Sep. 3, 2019

(54) TRACK PIN COMMUNICATION SYSTEM AND METHOD

(71) Applicant: Caterpillar Inc., Peoria, IL (US)

(72) Inventors: David W. Baarman, Fennville, MI (US); Brian B. Steketee, Grand Rapids, MI (US); Kevin Stephens, Bruceville, IN (US)

(73) Assignee: Caterpillar Inc., Deerfield, IL (US)

( * ) Notice: Subject to any disclaimer, the term of this patent is extended or adjusted under 35 U.S.C. 154(b) by 211 days.

(21) Appl. No.: 15/458,181

(22) Filed: Mar. 14, 2017

(65) Prior Publication Data
US 2017/0261450 A1    Sep. 14, 2017

Related U.S. Application Data

(60) Provisional application No. 62/307,819, filed on Mar. 14, 2016.

(51) Int. Cl.
| | |
|---|---|
| *G01N 25/72* | (2006.01) |
| *B62D 55/21* | (2006.01) |
| *H01L 35/32* | (2006.01) |
| *B62D 55/32* | (2006.01) |
| *H04W 4/80* | (2018.01) |

(52) U.S. Cl.
CPC ............ *G01N 25/72* (2013.01); *B62D 55/21* (2013.01); *B62D 55/32* (2013.01); *H01L 35/32* (2013.01); *H04W 4/80* (2018.02)

(58) Field of Classification Search
CPC .......... G01K 13/00; G01K 1/14; G01K 1/024; G01K 2205/00; B62D 55/21; B62D 55/32; G01N 25/72
USPC ............................ 374/141, 120; 340/870.17
See application file for complete search history.

(56) References Cited

U.S. PATENT DOCUMENTS

| | | | | |
|---|---|---|---|---|
| 1,371,628 | A * | 3/1921 | Kohler | B60K 3/00 165/115 |
| 2,138,317 | A * | 11/1938 | Weiss | F27B 9/243 198/851 |
| 8,098,147 | B2 * | 1/2012 | Fu | B60T 17/18 340/445 |
| 8,573,840 | B2 * | 11/2013 | Belandia | G01K 1/024 374/170 |
| 2015/0337522 | A1 | 11/2015 | Diekevers et al. | |
| 2017/0240046 | A1 * | 8/2017 | Vik | B60K 31/00 |
| 2018/0364744 | A1 * | 12/2018 | Garvin | E02F 9/02 |

FOREIGN PATENT DOCUMENTS

| | | |
|---|---|---|
| KR | 2015 0142460 | 12/2015 |
| WO | WO201760794 A1 * | 9/2017 |

OTHER PUBLICATIONS

International Search Report and Written Opinion of the International Searching Authority for International Application No. PCT/US17/22242 dated Jun. 5, 2017.

* cited by examiner

*Primary Examiner* — Gail Kaplan Verbitsky

(57) ABSTRACT

A track pin sensor for monitoring an operational status of a track pin of a track chain for heavy equipment. The track pin sensor may be incorporated into a communication system for monitoring a plurality of track pins of the track chain. A method of monitoring operational status of a track pin is also disclosed.

15 Claims, 15 Drawing Sheets

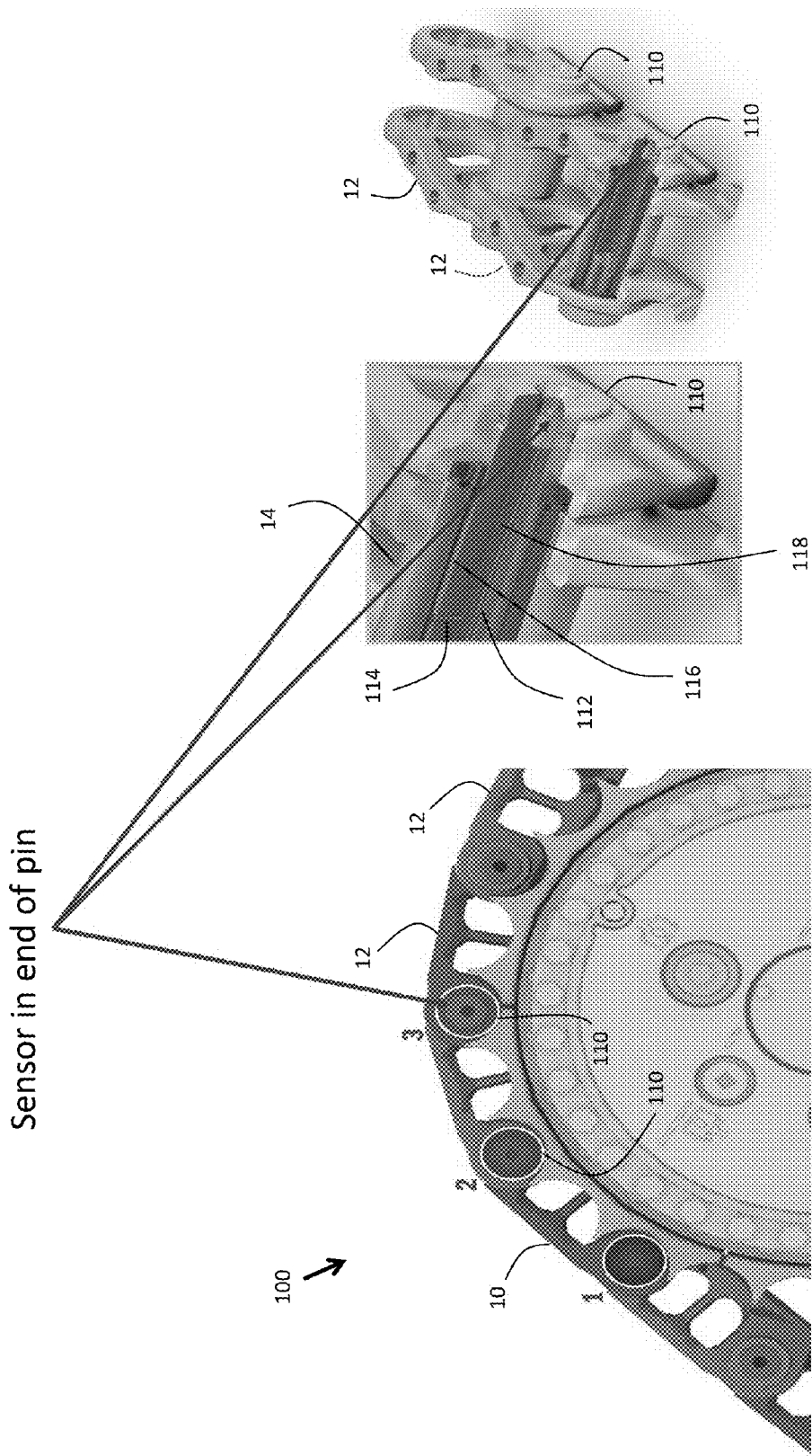

Touchless Wear Monitoring

Fig. 7 Self powered sensor hub and nodes

Sensor Node

Using heat pipes to create a differential temperature and remove heat

Using phase change materials to slow the equilibration of our differential temperature

Wear failure over time

| Time of wear | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| DeltaT | 10 | 10 | 10 | 10 | 10 | 10 | 10 | 10 | 10 | 12 | 14 | 18 | 24 | 30 | 38 | 48 | | | |

Failure event over time

| Time of wear | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| DeltaT | 10 | 10 | 10 | 10 | 10 | 10 | 10 | 10 | 10 | 10 | 10 | 48 | | | | | | | |

TRACK PIN COMMUNICATION SYSTEM AND METHOD

TECHNICAL FIELD

The present application relates to a system and method for communicating information wirelessly from a track pin to a remote device, and more particularly toward providing a communication system for one or more track pins in the field of track chains for heavy equipment.

BACKGROUND

Chains are a nearly ubiquitous component of the mechanical realm, and have been around for ages. Chains are most often comprised of a series of interlocking links or chain links. And in many cases, adjacent links are coupled together by a pin that slides through corresponding apertures of the adjacent links. This type of interlocking chain system is used in a variety of applications, including track chains for heavy equipment. As an example, heavy equipment, such as an excavator or a bulldozer, may include a set of track chains or track groups that include a plurality of links and associated track shoes driven about one or more hubs. The track chains can facilitate forward motion, reverse motion, and turning of the heavy equipment. Segments, sections, or links of this type of track chain are interlocked together via a type of pin often described as a track pin.

During periods of use, the components of the track chain often wear and sometimes fail. Due in part to the forces involved in heavy equipment and the rotational friction between the surface of the track pin and surrounding surfaces, the connection between adjacent links is a possible failure point. Efforts have been made toward enhancing the robustness of the connection between adjacent links, including utilizing sealed and lubricated type connections to yield a track chain that is often described as a Sealed and Lubricated Track (SALT). An example of a conventional track pin-based connection for the SALT configuration is shown in a sectional view in the illustrated embodiment of FIG. 16. Each of the links are coupled together primarily by a track pin and a stepping bushing. In many configurations, the track pin is press fitted through an aperture of the stepping bushing and outer apertures of one of the links. To reduce internal friction between the bushing and the track pin, the track pin in the example embodiment of FIG. 16 is provided with an oil reservoir and an oil passage in fluid communication with the mechanical interface between the track pin and the bushing. This configuration may lengthen the usable life of the connection—but, for a variety of reasons, such as normal wear and tear, the connection can fail or degrade to the point of imminent failure.

It should be understood that not all track chain configurations use a SALT type system. Rather, the SALT type system is described herein to facilitate understanding of a track pin-based track chain for a heavy vehicle or heavy equipment.

SUMMARY OF THE DESCRIPTION

The present disclosure is directed to a track pin sensor for monitoring an operational status of a track pin of a track chain for heavy equipment. The track pin sensor may be incorporated into a communication system for monitoring a plurality of track pins of the track chain. A method of monitoring operational status of the track pin is also described.

In one embodiment, the track pin sensor may be configured to monitor an operational status of the track pin, and may be at least partially disposed within a void of the track pin. The track pin sensor may include a temperature sensing element configured to provide an output indicative of a temperature characteristic of the track pin, and a wireless transmitter configured to communicate information to a remote device. The information may be indicative of an operational state or status of the track pin. The track pin sensor may include a controller operably coupled to the temperature sensing element and the wireless transmitter. The controller may be configured to determine the information based on the output of the temperature sensing element.

In another embodiment, the temperature sensing element may be a thermoelectric generator configured to supply power to the wireless transmitter and the controller to facilitate communication of information indicative of an operational state or status of the track pin, and where a voltage output of the thermoelectric generator is indicative of a temperature characteristic of the track pin. The track pin sensor may remain dormant until after a failure condition or abnormal condition presents in the track pin that is sufficient to generate enough heat to power the thermoelectric generator.

In yet another embodiment, the track pin sensor may form part of a communication system in which a plurality of track pin sensors, at least one remote device, and at least one user device communicate to provide and track operational status information of a plurality of track pins of the track chain. As an example, the user device may aid configuring the communication system by physically mapping each track pin sensor to a track pin of the track chain. The configuration process may include a user operating a test probe that provides sufficient heat to conduct a targeted activation of each track pin sensor, and performing the targeted activation in conjunction with a mapping process. In this way, each track pin sensor may be identified in connection with a specific track pin.

In still another embodiment, a method of detecting status information about a track pin of a track chain for heavy equipment may include providing a track pin sensor in a void of the track pin, where the void is substantially sealed and filled with lubricating oil. The method may include sensing with the track pin sensor a temperature characteristic of the track pin, determining status information based on the temperature characteristic, and wirelessly communicating the status information to a remote device.

The track pin sensor or the communication system, or a combination thereof, according to one embodiment may facilitate identification of potential failure conditions or abnormal operation conditions with respect to a track pin or surrounding structures that interface with the track pin, or both. These and other advantages and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 1 shows a track chain system and a communication system according to one embodiment;

FIG. 2 shows one or more chain sections of the track chain system;

FIG. 17 shows wear failure and failure event tables according to one embodiment, including temperature rises or differentials over time and thresholds for wear failure and failure events.

DESCRIPTION

Figure 18:
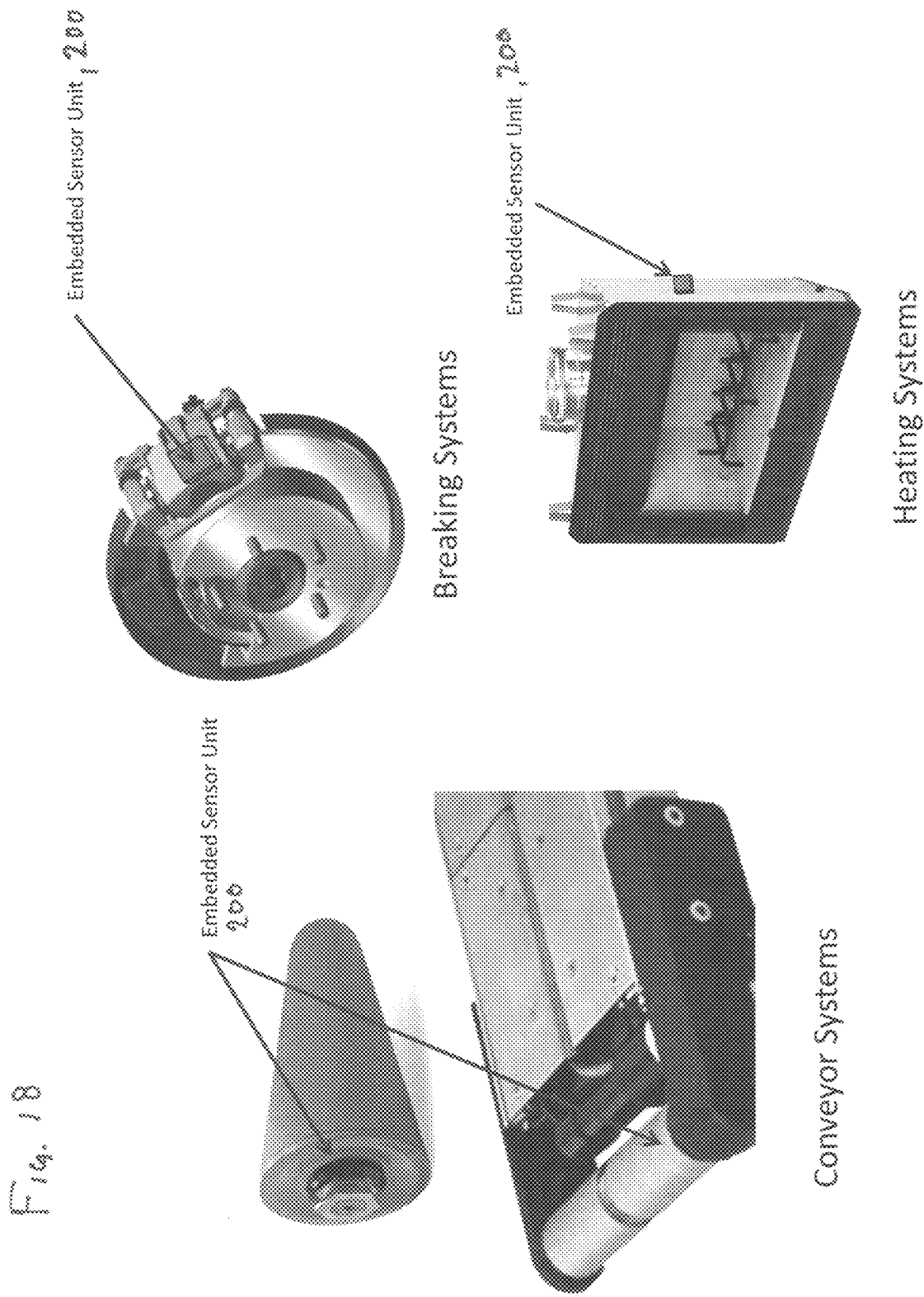
FIG. 18 shows a sensor according to one embodiment of the present disclosure configured to sense one or more operational characteristics in a variety of applications.

A communication system for a chain system, more particularly a vehicle track chain, is shown in FIGS. 1-6 and generally designated 100. The communication system 100 may be incorporated into a vehicle track chain 10, depicted in FIGS. 1-3 as a track chain for providing traction to drive a vehicle, such as heavy vehicle equipment, but is not so limited. The communication system 100 may be incorporated into any type of chain or rotating system or a system with a heat source, including systems not used for a vehicle or providing traction. Indeed, the track pin sensor may be used in connection with any type of pin, bearing, bushing, or rotating assembly, including engines and transmissions. Further examples are depicted in the illustrated embodiments of FIG. 18, which includes a sensor disposed in conjunction with a conveyor system, a braking system, and a heating system. In the illustrated embodiment of FIGS. 1 and 3, the vehicle track chain 10 includes a plurality of links 12 or track sections, adjacent ones of which are coupled together at least in part by a track pin 110. To the extent additional components that form the coupling between adjacent links 12, such as the bushing, thrust ring, and ring seal, are not described in further detail herein, these components are considered conventional and therefore no effort is given to elaborate on their construction and operation.

In the illustrated embodiment of FIG. 2, the track pin 110 is shown in further detail and may include an internal void 112 adapted to accept a track pin sensor, such as the track pin sensor shown and described in connection with the illustrated embodiment of FIG. 8 and generally designated 200. The internal void 112 of the track pin 110 may be an oil reservoir that is in fluid communication with an outer bearing surface 116 of the track pin 110 via an oil passage 114. In the illustrated embodiment, the outer bearing surface 116 may mechanically interface with a bushing 14 during operation. This mechanical interaction during operation, although possibly lubricated by oil, may generate heat due to friction. It should be understood that the internal void 112 is not limited to constructions that utilize an oil reservoir, and that the internal void 112 and the track pin 110 may be configured differently, such as an oil impregnated pin with no oil reservoir.

A plurality of track pins 110 and respective track pin sensors 200 may be disposed to join a plurality of track sections 12. In one embodiment, the track pins 110 may be specifically configured to interface with the track pin sensor 200. However, the present disclosure is not so limited—one or more of the track pins 110 may be conventional track pins, and the track pin sensor 200 may be adapted to interface with such a conventional track pin. In this way, a conventional track pin and a conventional track chain may be retrofitted with one or more track pin sensors 200 and the communication system 100. It should be understood that it is not strictly necessary for each junction between track sections 12 to include a track pin 110 with a track pin sensor 200, and that, for example, a conventional track pin without a track pin sensor 200 may be used to replace a failed track pin 110.

As described herein, the track pin sensor 200 may communicate information wirelessly to a remote device 150. Examples of the type of information communicated from the track and sensor 200 include sensor information, such as temperature or voltage generated by a thermal electric generator, an identification code or an ID, a communication identifier or a transmission count, and Ack/Nak verification information, or a combination thereof. Additional examples include information relating to a status of the track pin sensor 200 or information relating to an operating condition of the track pin 110, such as a wear indication or a warning about abnormal operation.

The track pin sensor 200 according to one embodiment may utilize the thermal energy produced in response to a failure event in order to provide thermoelectric generation of power. This thermoelectric generated power may be used to power components of the track pin sensor, such as a microprocessor, temperature sensor for temperature verification and a BTLE transmitter to send the sensor information of temperature, voltage generated, ID, number of transmissions, and Ack/Nak verification information. The environment and space for the track pin sensor 200 may limit the overall construction, as the track pin sensor is likely to be disposed in a very destructive environment. As mentioned above, the track pins 110 of heavy equipment may be filled with oil that is distributed to the pin and bushing wear surfaces over time. The hollow pin center or void 112 is a reservoir for that oil. A rubber stopper 234 may operate as a seal, and often includes a clear plastic plug or oil plug that allows filling of the reservoir. After filling the reservoir with oil, the plug may be pounded into the rubber stopper sealing the oil in place. This cavity or void 112 can be pressure tested at the factory to assure proper fit. Over time the oil may distribute through a hole or oil passage in the center of the track pin 110 relating to the center of the bushing 14. When the track pin 110 and bushing 14 wear, the bearing surfaces allow more friction, and this may create heat. Heavy equipment can benefit from knowing when such heating occurs because the heating may be indicative of a potential failure mode. By monitoring multiple effects of a potential failure mode, preventative maintenance may be enabled. For example, if detected early, components, such as the bushing 14 or track pin 110 can be changed or lubricated for longer life. As another example, a pressure test may be used to detect fit or lack of proper fit if a failure mode is detected. Additionally, by tracking sensed information, an understanding may be developed with respect to the effects of operation, and levels of failure may be identified based on energy levels and temperatures that would likely cause conventional batteries to fail.

The communication system 100 according to one embodiment may include a remote device, such as the remote device shown and described in connection with the illustrated embodiments of FIGS. 3-6 and generally designated 150. One or more remote devices 150 may be disposed in proximity to one or more vehicle hubs of the vehicle, and may, for example, be incorporated into the vehicle hub. In the realm of vehicle track chains for heavy equipment, several remote devices 150 may be disposed about areas of the track chain 10, including, for example, a front idler 20, a drive sprocket 22, a top roller 24, one or more lower rollers 26 and the rear idler 28, which form part of the vehicle track drive system. A remote device 150 may be disposed at or near a hub of each of these rotating components, and near which the track pins 110 travel as the track chain 10 travels. Due at least in part to the potential close proximity to the track pin sensors 200 as they travel with the track chain 10, communication between track pin sensors 200 and a remote device 150 may be achieved at lower power transmission levels. As an example, if a track pin sensor 200 detects that a track pin 110 is experiencing abnormal operating conditions, the track pin sensor 200 may communicate with each remote device 150 that the track pin 110 passes while traveling with the track chain 10. The communicated information to each remote device 150 may be indicative of the abnormal operating condition.

The communication system 100 may also include a user device 180 configured to receive and/or transmit information to one or more remote devices 150 disposed on the vehicle. The user device 180, itself, may be disposed on the vehicle, such as in a cab of heavy equipment. Alternatively, or additionally, the user device 180 may be a portable device carried by a user, such as a mobile phone or a key fob. The user device 180 may interface with the one or more remote devices 150 and provide status information or operating condition information to the user with respect to one or more track pins 110 and respective track and sensors 200. In this way, the user may be informed of potential failures or abnormal operating conditions with respect to track pins 110 of the track chain 10. Based on this information, the user may take proactive steps to replace one or more track pins 110 prior to possible failure. In other words, with a plurality of track pins 110 and respective track pin sensors 200 disposed at connections between track sections 12 of the track chain 10, and the capability to inform a user about operating conditions, the communication system 100 according to one embodiment may facilitate proactive maintenance.

I. Track Pin Sensor

The track pin sensor 200 according to one embodiment of the present disclosure is shown and described in connection with the illustrated embodiments of FIGS. 8 and 9. The track pin sensor 200 may be adapted to fit within the void 112 of the track pin 110, and may be self-powered by a thermoelectric generator 202. The track pin sensor 200 may further include an antenna 204 and sensor circuitry 206. The sensor circuitry 206 may include one or more components configured to interface with the thermoelectric generator 202 and the antenna 204, enabling the sensor circuitry 206 to receive power from a thermoelectric generator 202 and communicate information wirelessly via the antenna 204. In one embodiment, the sensor circuitry 206 may include a power supply 210, a communication interface 214, such as a BlueTooth Low Energy (BLTE) transceiver, a microprocessor 212, sensor inputs 216, and nonvolatile memory 218. It should be understood that one or more of these components may be integrated into a single component, such as a controller or microprocessor configured to include a BLTE transceiver, sensor inputs and nonvolatile memory.

In one embodiment, the track pin sensor 200 may be integrated with a rubber stopper 234 that at least partially seals the void 112 of the track pin 110 to substantially prevent oil leakage from the void 112 or oil reservoir. The rubber stopper 234 may be adapted to receive an oil plug in an oil plug hole 236, which may be configured to operate in conjunction with the oil plug to increase the sealing pressure of the rubber stopper 234 against the interior surface 118 of the track pin 110, facilitating substantial prevention of oil leakage.

The antenna 204 may extend at least partially through the rubber stopper 234 to facilitate wireless communication by positioning a portion of the antenna outside the void 112 or closer toward an exterior of the track pin 110. In the illustrated embodiment, the antenna 204 is surrounded at least partially by the rubber stopper 234, and extends therethrough to interface with ambient air. This configuration may facilitate effective transmission of wireless communication at lower energy levels.

The track pin sensor 200 may include a hot side conductor 230 and a cold side conductor 232 that may be in thermal communication with the thermoelectric generator 202 to provide a temperature differential across a hot side surface 240 and a cold side surface 242 of the thermoelectric generator 202. These conductors 230, 232 may be copper and over-molded into the rubber stopper 234.

The hot side conductor 230 may be thermally coupled to an interior surface 118 of the track pin 110 that defines the void 112. This interior surface 118 may be heated in use, due at least in part to friction between the track pin 110 and other components, such as the bushing 14, that provide the connection between links 12 of the vehicle track chain 10. Thermal coupling between the hot side conductor 230 and the interior surface 118 may be achieved via direct contact, such by utilizing spring-like connections to maintain a thermal coupling with the interior surface 118.

The cold side conductor 232 may be at least partially disposed within the void 112 and thermally coupled to the cold side surface 242 of the thermoelectric generator 202. The cold side conductor 232 may be disposed to be at a different, lower temperature than the hot side conductor 230, and may be substantially thermally isolated via insulation 250 from direct thermal coupling with the interior surface 118 of the track pin 110 or the oil therein. For instance, at least a portion of the cold side conductor 232 may be thermal insulated by the insulation 250 from oil and the interior surface 118, and at least another portion of the cold side conductor 232 may be directly thermally coupled to ambient air, which is lower in temperature than the interior surface 118 of the track pin 110. With the temperature differential across the hot side surface 240 and the cold side surface 242, the thermoelectric generator 202 may produce power sufficient to power one or more components of the track pin sensor 200, or to provide an indication of a temperature differential being present across the thermoelectric generator 202, or a combination thereof. In this way, a track pin sensor 200 according to one embodiment may not be fully powered from a battery, which in some cases may be too large to fit within the void 112 or not rated for the amount of thermal energy generated within the void 112 in use.

Put differently, the thermoelectric generator 202 may be adapted to harvest energy, and to withstand more thermal energy than a conventional battery or a conventional supercapacitor, or both. For instance, the amount of heat present within the void 112 may be sufficient to destroy a conventional battery or conventional supercapacitor. By utilizing the thermoelectric generator 202, the track pin sensor 200 according to one embodiment may achieve a self-powered configuration under extreme temperatures. Conditions that present thermal energy too large for a conventional battery may be taken advantage of by generating power and potentially avoiding a separate power source, thereby reducing size and enhancing reliability. Further, because the size of a conventional battery, in some cases, may be impractical for use within the void 112, the thermoelectric generator 202 may enable the track pin sensor 200 to be utilized in connection with smaller track pins 110 than would be possible with a large battery source.

In the illustrated embodiment, the sensor circuitry 206 of the track pin sensor 200 may be insulated via the insulation 250 along with at least a portion of the cold-side conductor 232. The insulation 250, in one embodiment, may form at least part of an enclosure for the thermoelectric generator 202 and the sensor circuitry 206. The enclosure may be oil proof to substantially prevent oil leakage and direct thermal coupling with oil. The insulation 250 may include a protective coating that is oil resistant and does not conduct heat well, such as Master bond ep21pnd or 3M Novec electronics grade coatings.

In one embodiment, as described herein, the output from the thermoelectric generator 202 may be used as an indicator of a thermal condition of the track pin 110. For instance, if the amount of heat being generated by one or more of the mechanical interfaces around the track pin 110 is sufficiently large such that the thermoelectric generator 202 is presented with a temperature differential sufficient to yield power from the thermoelectric generator 202, the thermoelectric generator 202 may both provide a signal indicative of the thermal condition as well as power to activate circuitry of the track pin sensor 200.

In one embodiment, such a thermal condition may be the only mode in which the track pin sensor 200 is active or enabled to communicate an event or information to a remote device. For instance, the power generation may enable the track pin sensor 200 to be powered and then sends an ID and the sensor data, temperature, and voltage, or a combination thereof. As described herein, the track pin sensor 200 may resend information to a remote device until the track pin sensor 200 receives an acknowledgment receipt from the remote device. The track pin sensor 200 may then wait for a period before resending the information again but will continue until the track pin sensor 200 cools off, or the thermal condition that enabled power generation from the thermoelectric generator 202 is not present. The excess energy is accumulated between transmission of information, and may be used to flash an LED through a clear oil sealing pin. In this way, the flashing LED may provide a visual indication of the thermal condition being present, e.g., the sensor tripping. In one embodiment, the flashing LED may indicate that a signal transmission has been verified or acknowledged by the remote device 150.

In one embodiment, the track pin sensor 200 may activate a persistent visual element to change state in response to detection of a potential failure mode or abnormal operating condition. In this way, the track pin sensor 200 may indicate a state change even in cases where sufficient power to activate is only transitory and available for a short period of time.

As described herein, the thermoelectric generator 202 may generate energy based on the temperature differential present between the hot side conductor 230 and the cold side conductor 232. This type of energy generation is based on the principles behind the Peltier effect and the Seebeck effect. The Peltier effect is considered production of a temperature difference by applying a voltage between two electrodes connected to a sample of semiconductor material. This phenomenon can be useful to transfer heat from one medium to another on a small scale. The Seebeck effect is generally the reverse of the Peltier effect: production of voltage or power by applying a temperature differential across the sample of semiconductor material. The Seebeck effect and the Peltier Effect take advantage of thermal energy, that is, in many cases, a byproduct of other forms of energy such as chemical energy, mechanical energy, and electrical energy. The process in which electrical energy is transformed into thermal energy is called Joule heating. This is what can cause wires to heat up when current runs through them. Examples of conventional thermoelectric generators can be purchased from TEG Power, an apparent subsidiary of LED Dynamics.

Another type of thermal-based generator that may be utilized as the thermoelectric generator 202 in one or more embodiments includes a MEMS based thermoelectric power generator. MEMS based thermoelectric devices may transform waste heat into electricity and may be used in the track pin sensor 200. One such type of MEMS based thermoelectric generator is the MEMS generator developed by Oak Ridge National Laboratory (ORNL). The ORNL MEMS generator has been shown to achieve approximately 14 percent efficiency at converting heat into electricity in a package size that is substantially smaller than that of many conventional batteries. The ORNL MEMS generator uses small, 1 square millimeter-sized cantilever structures to build a device that is not thermoelectric at its core but whose basic elements can produce 1 to 10 milliwatts each. If 1,000 of these devices are stacked onto a 1-inch square surface, the power output may be scaled up and the electricity obtained may be used to drive the track pin sensor 200.

Figure 8:
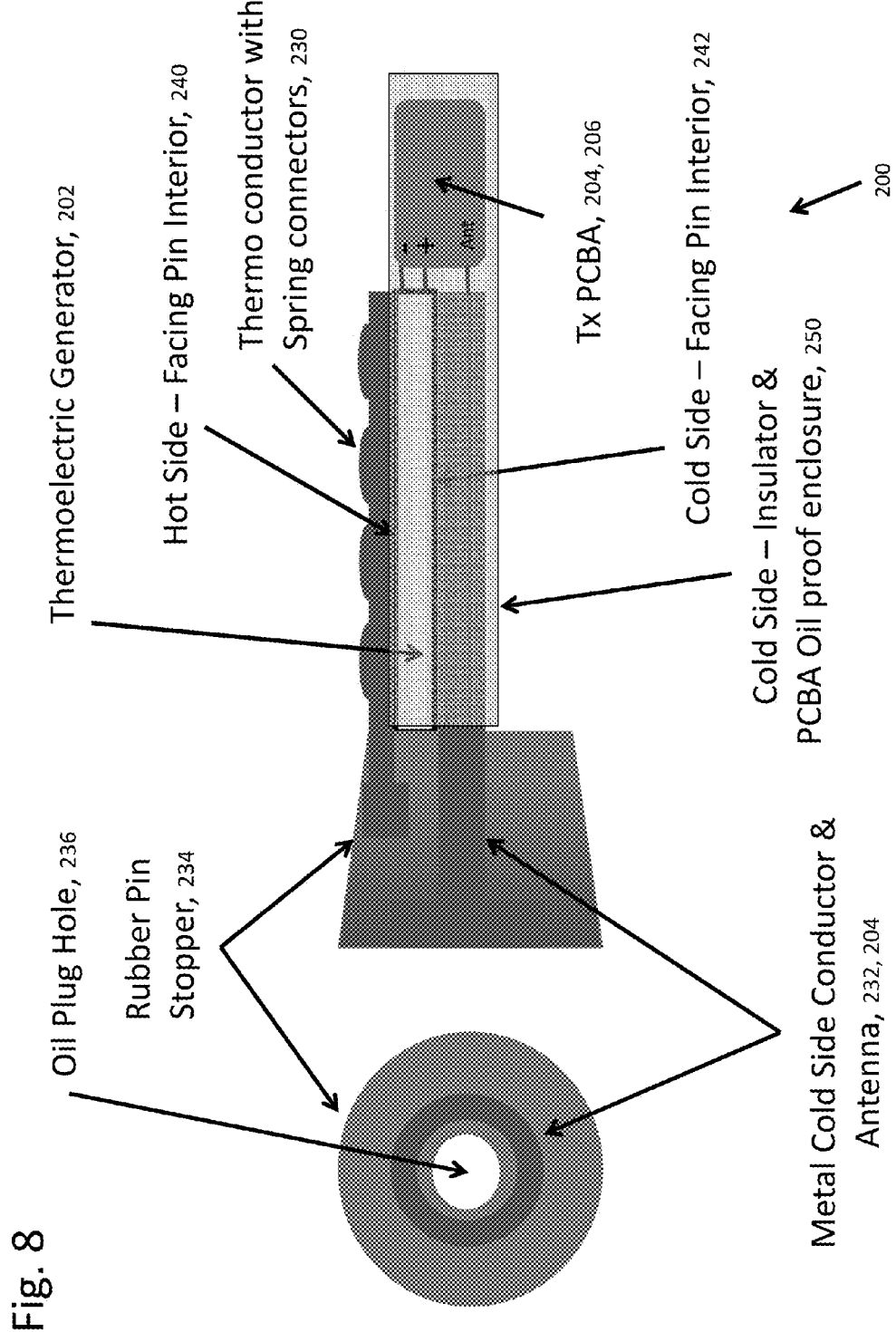
FIG. 8 shows a representative view of a track pin sensor according to one embodiment.
Figure 9:
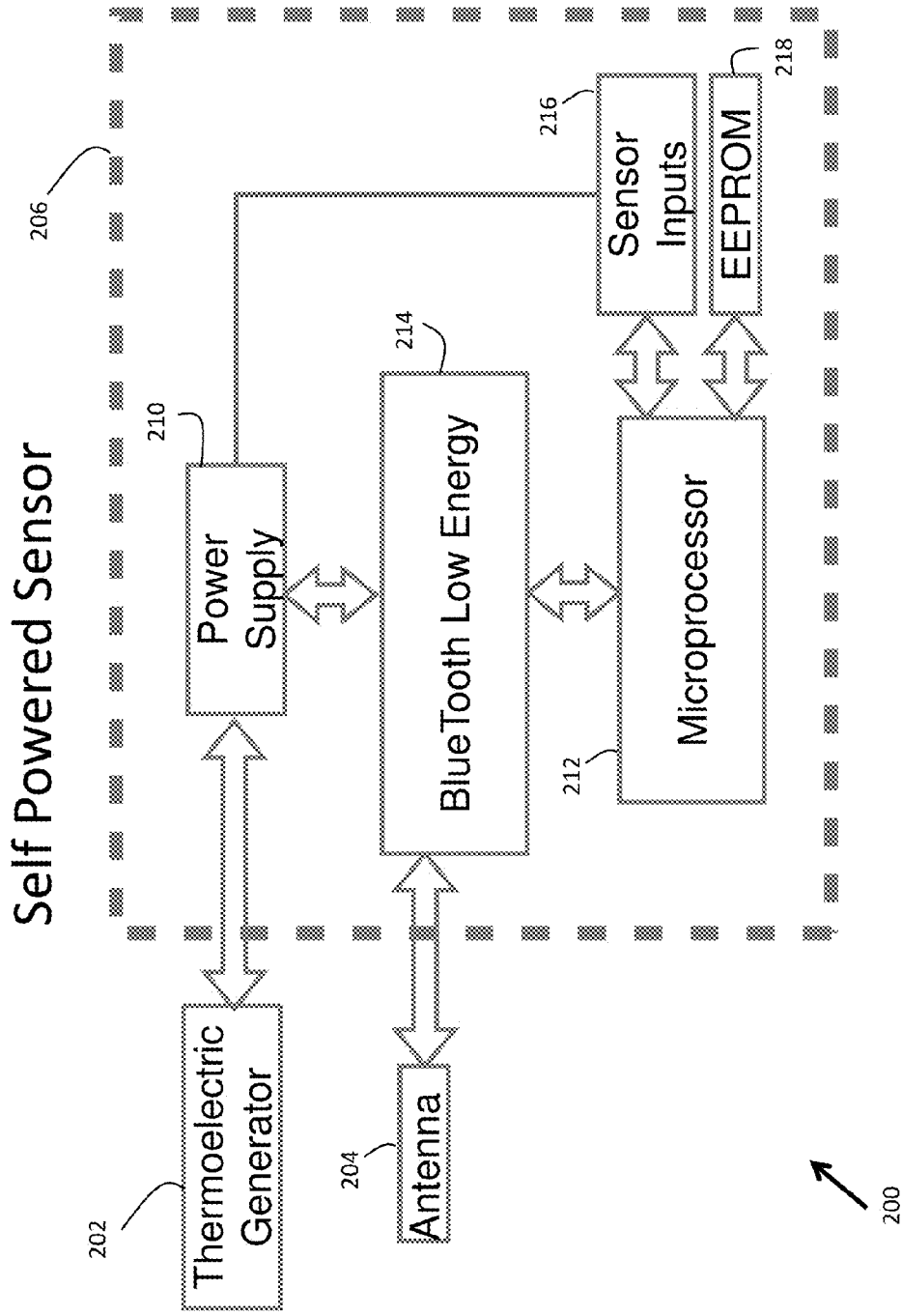
FIG. 9 shows a representative electrical diagram of the track pin sensor of FIG. 5.

It should be understood that the track pin sensor 200 in the illustrated embodiment of FIGS. 8 and 9 is not limited to being self-powered by a thermoelectric generator 202, and that other power sources may be utilized alone or in conjunction with the thermoelectric generator 202, including, for example, one or more of a battery, a supercapacitor, and a wireless power supply.

A track pin sensor according to another embodiment is shown and described in connection with FIG. 12 and is generally designated 400. The track pin sensor 400 is generally similar to the track pin sensor 200, and includes a thermal electric generator 402, a hot side conductor 430, a cold side conductor 432, a power supply 410, a sensor 416, a controller 412, and a communication transceiver 414, similar respectively to the thermoelectric generator 202, the hot side conductor 230, the cold side conductor 232, the power supply 210, the communication transceiver 214, the microprocessor 212, and sensor inputs 216. In the illustrated embodiment of FIG. 12, the track pin sensor 400 includes a power storage element 411, such as a battery or capacitor. It should be understood that the power storage element 411 may be absent and power may be provided solely from the thermoelectric generator 402. In one embodiment, the power storage element 411 may include capacitance to provide power or facilitate accumulation of power to energize the track pin sensor 400 to communicate information. The energy capacity and type of storage device incorporated into the power storage element 411 may be depend on a variety of factors, including, for example, tradeoffs between amount of power capacity, overall size, and the maximum rate of energy storage.

In the illustrated embodiment, the thermoelectric generator 402 may operate as a type of temperature sensor providing a voltage differential indicative of a temperature sensed by the thermoelectric generator 402. The hot side conductor 430 may be thermally coupled to a heat or thermal source (or a potential heat source) of a mechanical arrangement, such as a track pin bearing, a conveyor system bearing, a braking system and a furnace system. A sensor according to one embodiment of the present disclosure may be used in conjunction with any type of mechanical system that generates heat. Additional examples include duct systems, semi-trailer brake systems, fan control over furnace systems, and radiator monitoring and reporting. In one embodiment, additionally or alternatively, the sensor may include one or more additional sensors, such as an accelerometer.

In the illustrated embodiment, the cold side conductor 432 may be thermally coupled to a heat sink that transfers thermal energy of the cold side conductor 432 to another medium, such as ambient air, water or metal. As an example, the cold side conductor 432 may be thermally coupled to the antenna 404, which, in turn, may be thermally coupled to ambient air. Further, in one embodiment, the antenna 404 may be configured to dissipate heat energy as well as transmit and receive communications. The cold side conductor 432 may be coupled directly to the antenna 404 or may be coupled indirectly via another thermal medium.

As described herein, the thermoelectric generator 402 and the track pin sensor 400 may be configured such that a failure point temperature provides a sufficient differential across the thermoelectric generator 402 to power the track pin sensor 400 to communicate the failure mode. In one embodiment, if the actual temperature is below the failure point temperature threshold, the track pin sensor 400 may remain dormant and unpowered. In this way, the track pin sensor 402 may become active only after conditions exceed an abnormal temperature or failure point temperature threshold.

In the illustrated embodiment, the location or distance, or both of the temperature inputs or thermal conductors in communication with the thermoelectric generator 402, may be varied from application to application. As an example, the thermoelectric generator 402 may be a long skinny design, but the size and length may vary from application to application, including wider/narrower constructions or longer/shorter constructions, or a combination thereof. It should be understood that different designs may have varied temperature ranges, although the primary temperature range is shown in Table 1. Further, the temperature inputs or thermal conductors may be configured such that power is generated in the thermoelectric generator 402 over a desired range of temperatures, or a minimum and maximum range of temperatures, including those identified in Table 1, in order to facilitate powering the track pin sensor 400 under select operating conditions, such as when abnormal modes or failure modes are present. For instance, if the temperature inputs or thermal conductors are configured for a range of temperatures below a normal operating temperature of the track pin 110, the track and sensor 400 may be operating and communicate information under normal conditions, and may be incapable of differentiating between normal and abnormal modes (e.g., the thermoelectric generator may be saturated, providing a constant output, or operating at its peak voltage). Alternatively, the thermoelectric generator may operate under normal operating conditions, and provide a sensor output that indicates both normal and abnormal operating conditions.

By configuring the temperature inputs and thermal conductors interface with the thermoelectric generator 402 to be indicative of failure or abnormal modes, the track pin sensor 400 may be configured to power up and indicate such modes to the remote device 150 when such modes are present. As an example, the temperature range of the temperature inputs and thermoelectric generator 402 may be selected such that the voltage output from the thermoelectric generator 402 is variable in a temperature range near the failure temperature threshold. In this way, the track pin sensor 400 may be configured to sense changes in temperature around the failure temperature threshold.

As described in connection with the track pin sensor 200, the temperature inputs, such as one or both of the hot side and cold side conductors, of the track pin sensor 400 may be resistant to degradation due to exposure to harsh conditions present in the oil or by being in contact with the interior surface 118 of the track pin 110. The thermoelectric generator 402 and other components of the track and sensor 400 may be disposed within an insulating enclosure 450 to substantially prevent degradation due to exposure to such harsh conditions.

Figure 15:
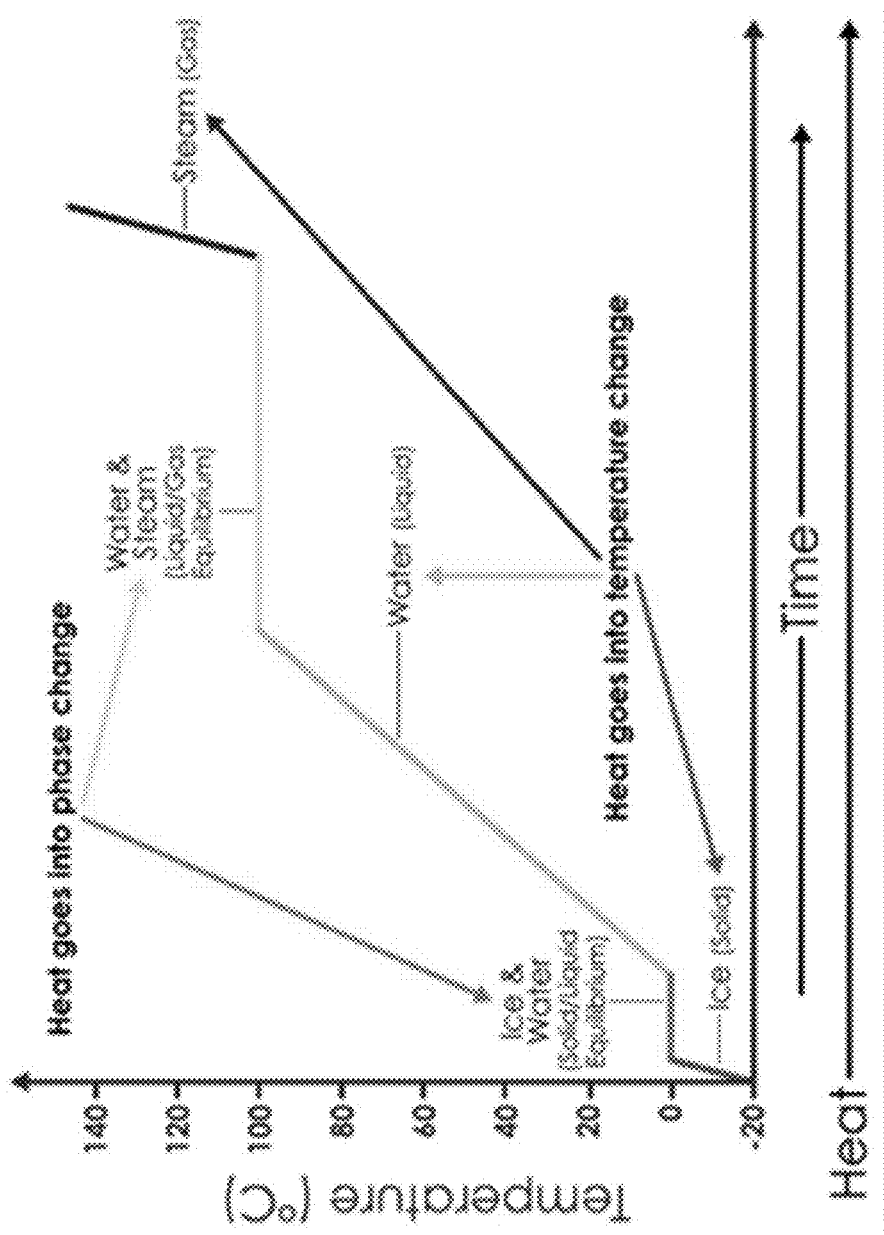
FIG. 15 depicts operational characteristics of phase change material.
Figure 16:
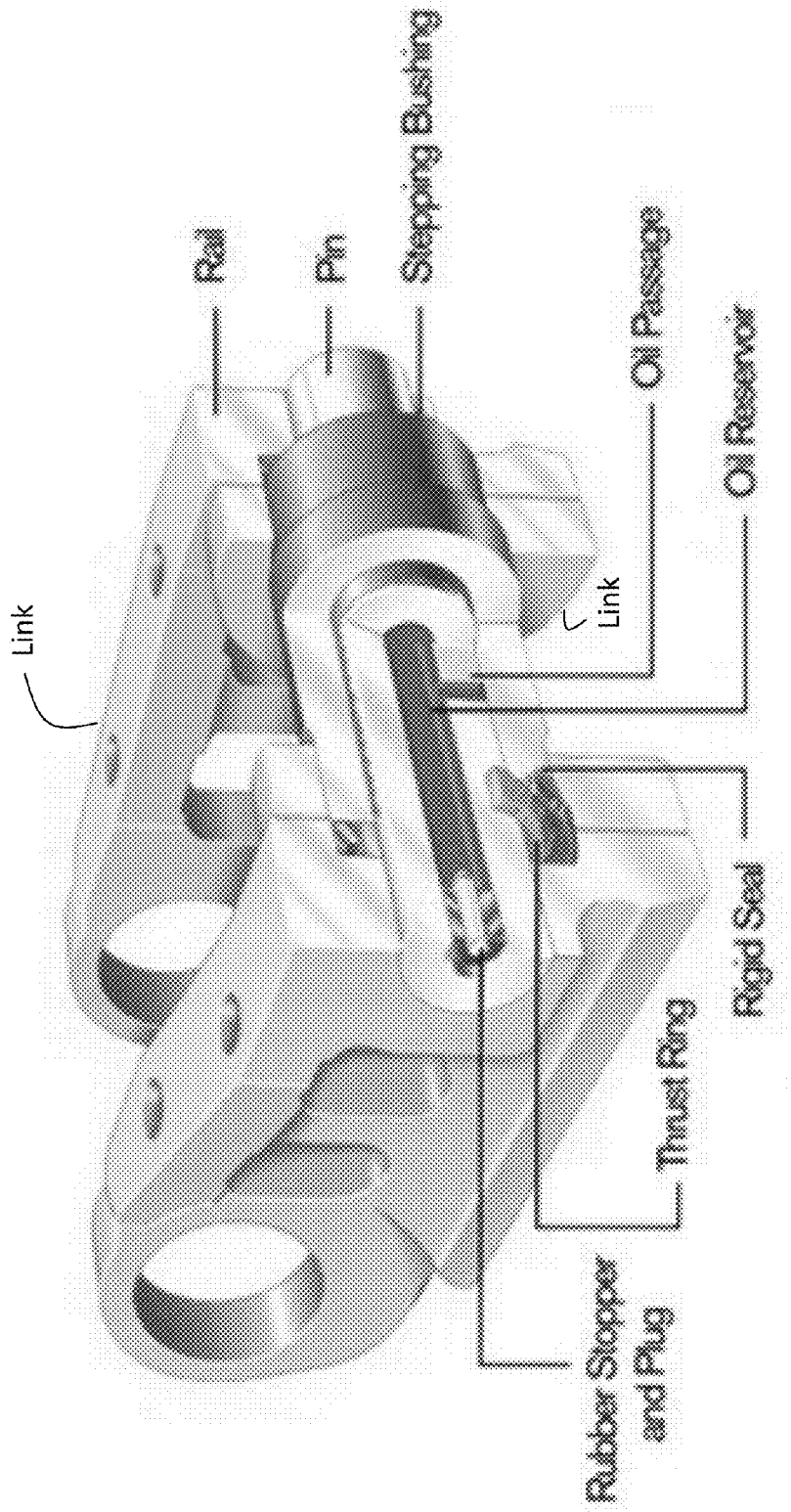
FIG. 16 shows a sectional view of a prior art track section including a conventional track pin.

In one embodiment, the hot side and cold side conductors 430, 432 of the track pin sensor 400 may be solid metal, such as copper or aluminum. Alternatively, or additionally, the hot side and cold side conductors may incorporate or be formed of a liquid-based heat exchanger or a phase change based system. A phase change-based system according to one embodiment is described herein in connection with FIG. 15.

The thermoelectric generator 402 of the track pin sensor 400 may form the bulk of the track pin sensor 400. As a result, there are trade-offs between size and power efficiency and total available power output. In general, depending on the construction of the track pin 110, the thermoelectric generator 402 may be configured to be as large as will possibly fit within the void 112 of the track pin 110. With this design consideration, the amount of available power output may enable a greater temperature range over which failure modes can be detected, and to power the track pin sensor 400 for longer durations.

The power supply 410 may include power management capabilities to utilize power output from the thermoelectric generator 402 in an efficient manner. For instance, the power supply 410 may be an energy harvesting power supply that produces a regulated power source based on voltage produced by the thermoelectric generator 402. The power supply in one embodiment may be powered solely from the thermoelectric generator 402. Alternatively, output from the power supply may be augmented through use of a separate power supply, such as a battery 411. In one embodiment, the power supply 410 may be powered solely from the battery 411, and the thermoelectric generator 402 may be utilized primarily as a temperature sensor. The power supply 410 may include a capacitor or other conditioning circuitry to regulate or accumulate power received from the thermoelectric generator 402 to drive circuitry of the track pin sensor 400. In the illustrated embodiment, the power supply 410 may be configured to provide a single output for powering all sensor components—but, it should be understood that multiple power domains may be utilized, and that the power supply 410 may provide multiple power outputs dependent on the component ratings, such as a 3.3V for some components and 5V for other components. The power supply 410 may also be configured to enable communication in an effective manner from the transceiver 414, such as the rated power amounts for transmitting from the transceiver according to its protocol (e.g., BLTE and duty cycle of operation for effective communication).

Although the track pin sensor 400 is described primarily in connection with utilizing a thermoelectric generator 402 as a temperature sensor, the track pin sensor 400 may additionally, or alternatively include one or more sensors 416, such as a dedicated temperature sensor. In the illustrated embodiment, in which both a dedicated temperature sensor and the thermoelectric generator 402 are used as a basis for determining temperature, the track pin sensor 400 may utilize the dedicated temperature sensor to further enhance precision of the temperature determined by the thermoelectric generator 402. It should be understood that the present disclosure is not limited to use of temperature sensors only, and that the one or more sensors 416 may be incorporated into the track pin sensor 400, and may include any type of sensor, including, for example at least one accelerometer, ambient temperature sensor, thermal source temperature sensor, temperature of the controller 412, and voltage.

Figure 12:
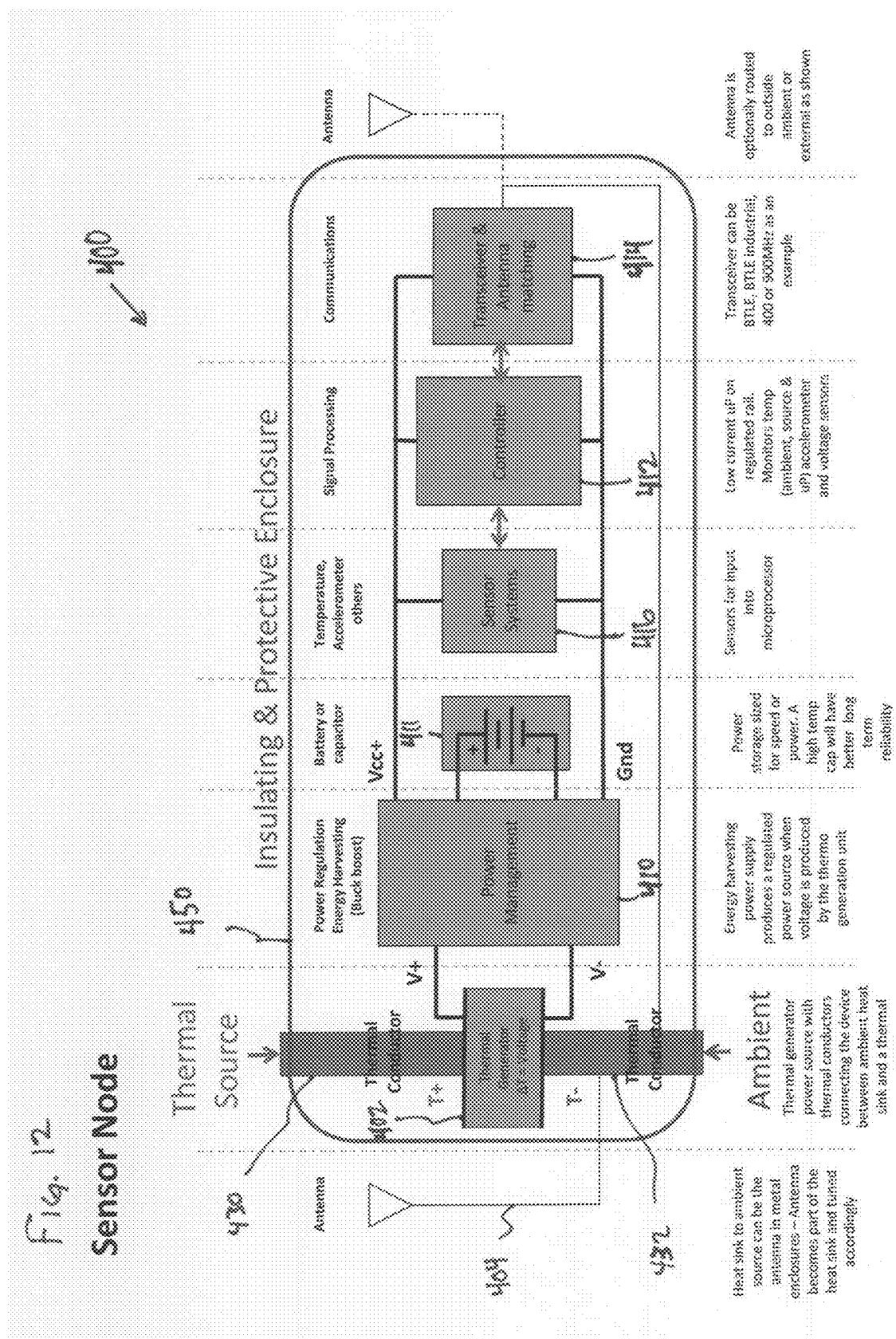
FIG. 12 shows a representative view of a track pin sensor according to yet another embodiment.

In the illustrated embodiment of FIG. 12, the controller 412 and the communication transceiver 414 are shown separate. But it should be understood that the components may be integrated, as described herein. The controller 412 may be in communication with at least one of the sensor 416 and a signal operably communicated from the thermoelectric generator 402 to indicate a sensed temperature. Based on this information, the controller 412 may communicate information, via the communication transceiver 414, to the remote device 150. As described above, the communication transceiver 414 according one embodiment may be a BTLE transceiver, a BTLE industrial transceiver (e.g., 400 MHz or 900 MHz). In one embodiment, the controller 412 may be a low current microprocessor that operates from the regulated rail provided by the power supply 410. The controller 412 may monitor outputs from the one or more sensors, such as the one or more sensors 416 and the voltage output from the thermal electric generator 402. The antenna 404, as described herein, may be optionally routed to outside ambient air or external to the insulating enclosure 450.

As should be apparent from the description herein of the principal operation of the thermoelectric generator 402, energy output from the thermoelectric generator 402 is dependent primarily on existence of a temperature differential between the temperature inputs. As depicted in the illustrated embodiment of FIG. 8 and described in connection with the illustrated embodiment of FIG. 12, the cold side conductors and circuitry of the track pin sensor 200, 400 may be insulated from the oil and features of the track pin 110. A rise in temperature over a period of time with respect to the hot side and cold side conductors may generate energy. Over time and despite presence of an insulator, in some embodiments, substantial temperature equilibrium may be reached between the hot side and cold side conductors, reducing the amount of available power. The track pin sensor 200, 400 may be configured to communicate information to the remote device 150 in the time over which the temperature differential exists and sufficient energy is present to power the sensor.

Figure 14:
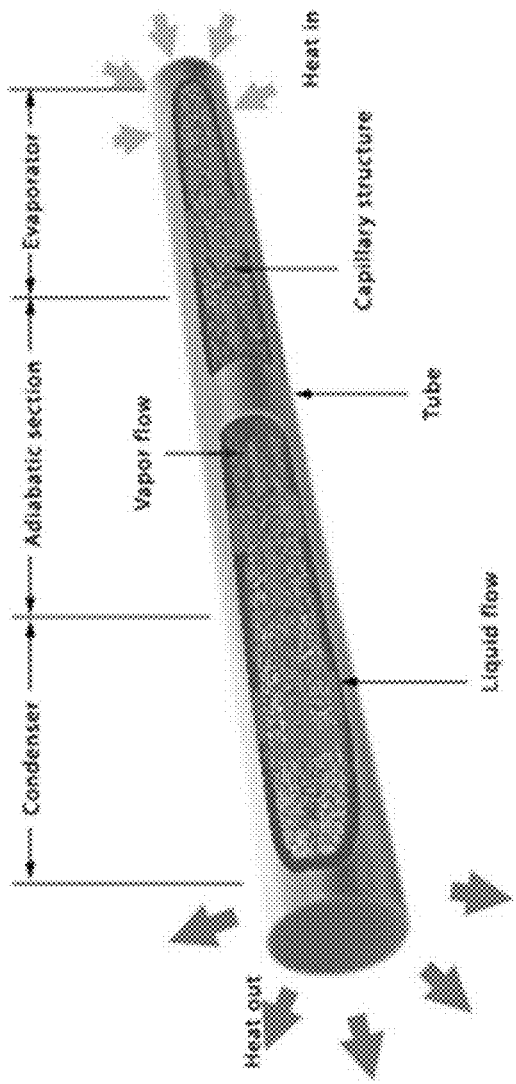
FIG. 14 depicts a heat pipe construction.

In one embodiment, the thermoelectric generator 202, the hot side conductor 230, and cold side conductor 232 may be configured to extend the temperature delta over time by substantially preventing the cold side from equilibrating from the hot side thermal energy. The factors that extend this delta in temperature and extend power over time may include the following: insulation of the cold side heat sink and allowing the heat to be removed efficiently. For instance, temperature equilibrium between the cold side and hot side conductors may be substantially avoided by arranging or configuring the cold side conductor to thermally conduct energy to a heat sink, such as a copper plate that facilitates convective transfer of heat to ambient air. As another example, the physical construction of the hot side and cold side conductors 230, 232 may be adapted to efficiently provide a temperature delta over a period of time. One such example can be seen in the illustrated embodiment of FIG. 14, which shows a heat pipe that may be used to remove heat from electronics components, such as the sensor circuitry 206, or the cold side of the electric generator 242. Such a heat pipe may enable efficient removal of heat, such as from the cold side conductor, to substantially maintain a temperature delta sufficient to generate power from a thermoelectric generator 202. The heat pipe may be used to increase the differential temperature and power by affecting the delta temperature across the thermoelectric generator. Additionally, or alternatively, a mechanical heat sink or a ventilated surface for convective thermal dissipation may be used to facilitate transfer of heat. As yet another example, the hot side conductor 230 or the cold side conductor 232, or both, may be formed of phase change materials that facilitate delay in temperature equilibration. Such phase change materials may absorb the energy until the material changes phases. The phase change may extend the temperature delta time, and enable sufficient power over time to send communications from the track pin sensor, including, for example, error signals and condition reports. Operational characteristics of such phase change material are shown in the illustrated embodiment of FIG. 15. In other words, the phase change material may be used to prolong the cold side temperature during equilibrium until the material changes phase. This effect may extend the amount of time until equilibrium and allow more time to communicate information.

The track pin sensor 202, 402, by utilizing a temperature differential for thermoelectric generation of power, may avoid use of a battery that, if used, may become depleted prior to existence of an abnormal condition or failure mode. The track pin sensor 202, 402 according to one embodiment system may send an error every time the differential temperature exists, and may track the temperature changes toward end of life.

Figure 11:
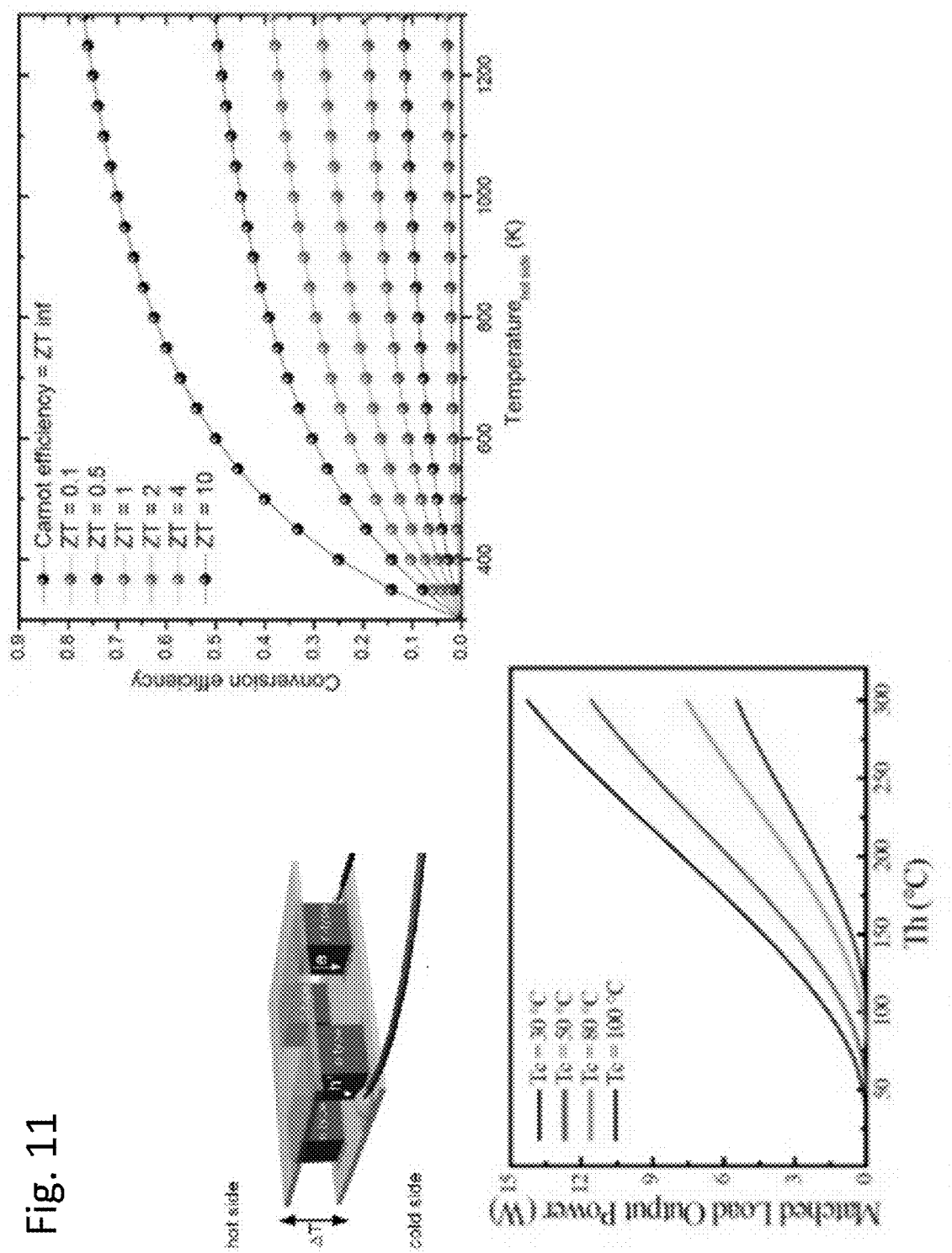
FIG. 11 depicts a thermoelectric generator and conversion characteristics for the same.

Example power output characteristics of a thermoelectric generator according to one embodiment are shown in the illustrated embodiment of FIG. 11. The thermoelectric generator in the illustrated embodiment is a one square inch device configured to supply sufficient power to power a small transceiver similar to the communication transceiver 214, 414 in the illustrated embodiment of FIGS. 8 and 12.

A track pin according to yet another embodiment is shown and described in connection with FIG. 10 and is generally designated 300. The track pin sensor 300 is generally similar to the track pin sensor 200 but with several exceptions. For example, the track pin sensor 300 may include sensor circuitry 306, a power supply 310 and an antenna 304, similar in many but not all respects to the sensor circuitry 206, power supply 210 and antenna 204. It should be understood that one or more features or functions described in connection with the track pin sensor 300 may be included in the track pin sensor 200 or the track pin sensor 400, and conversely one or more features or functions described in connection with the track pin sensors 200, 400 may be included in the track pin sensor 300. Further, one or more features or functions described in connection with any of the embodiments of the track pin sensor may be absent.

Figure 10:
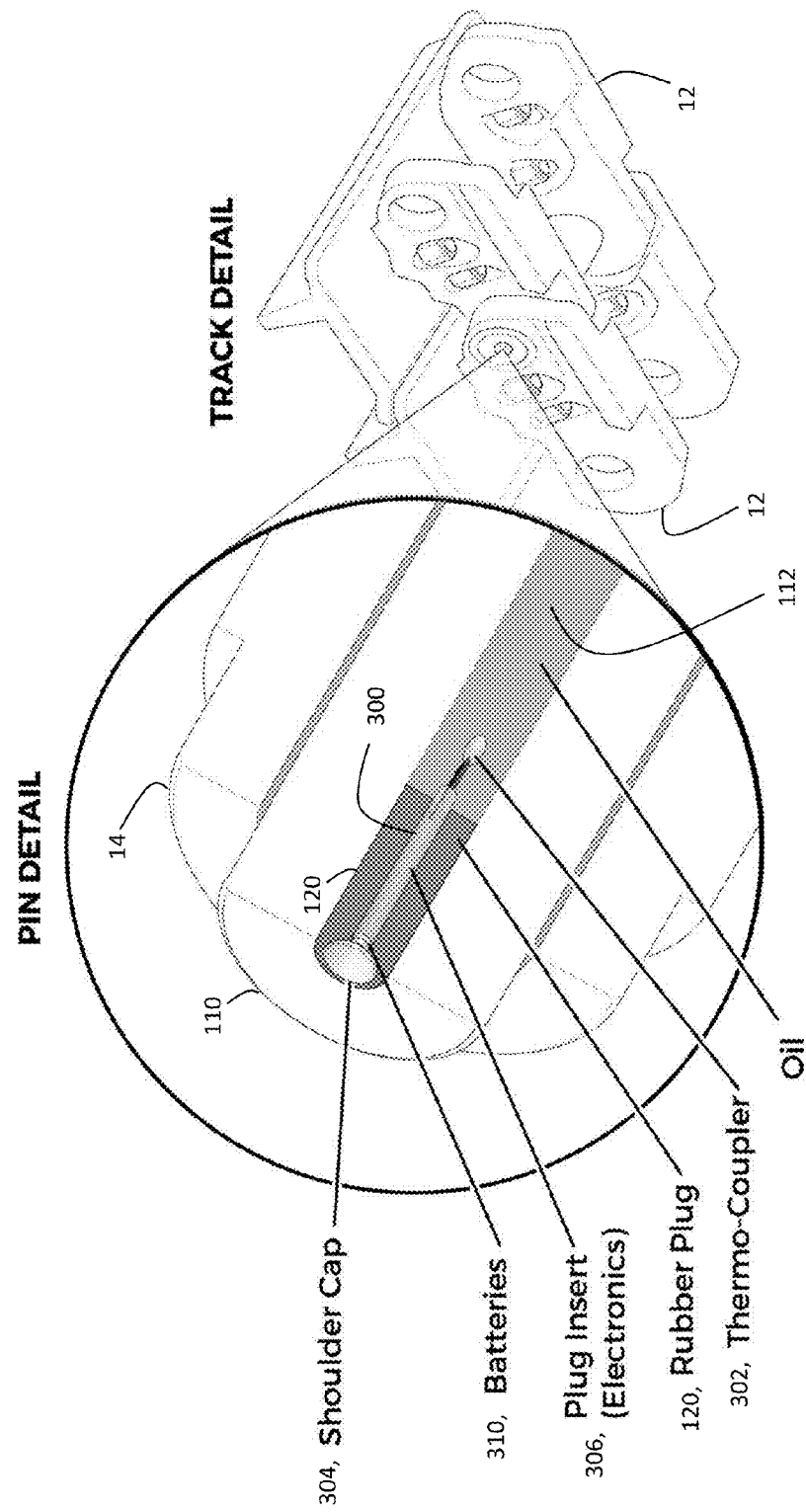
FIG. 10 shows a representative view of a track pin sensor according to another embodiment.

The track pin sensor 300 in the illustrated embodiment of FIG. 10 may include a thermocouple 302 configured to be disposed within the void 112 in which oil is present and to measure the temperature of the oil. The thermocouple 302 may operate in a manner similar to the thermoelectric generator (e.g., the thermoelectric effect) to provide a signal indicative of a temperature. An example of such a thermocouple is a K-type thermocouple. In the illustrated embodiment, the thermocouple 302 may be dedicated toward measuring temperature and being in direct contact with the oil. A thermistor or thermocouple, or both, may be used in addition for confirmation of operating temperature.

An example of the temperature delta and the temperature range for operation according to one embodiment are listed in Table 1 below.

TABLE 1

Example Temperature Range and Delta

Pin Temp Range - During Vehicle Operation - No Failure:
   Min −50 F.
   Max 180 F.
Pin Temp Range - During Vehicle Operation - Failure mode:
   Min 190 F. - Max Ambient + 10 F. Guard band (e.g., 10 F. hysteresis, a 10 F. error margin, or a 10 F. baseline)
   Delta-T or changes in T may be used as a basis for detecting early failures, including, for example, changes greater than 10 F. over a period of time
   Max 275 F. - Complete failure
Pin Delta-T - During Vehicle Operation - No Failure:
   ~10 F. from Ambient Another example of the temperature delta and the temperature range of operation according to one embodiment are depicted in the illustrated embodiment of FIG. 17. In the illustrated embodiment, wear failure and failure event sequences are shown, including multiple measurements of Delta-T over time. As shown in the wear failure sequence, the temperature delta or Delta-T remains around 10 F for the first nine measurements, and then gradually begins to rise. After the Delta-T passes 38 F but remains less than 59 F, the system 100 may determine there is a failure warning condition, and provide an indication of this condition to a user. After the Delta-T reaches and passes 59 F, the system 100 may determine there is a wear failure state, and provide an indication of the wear failure state to a user. It should be understood that the threshold temperatures in the wear failure sequence and failure event sequence may vary from application to application.

As shown in the failure event sequence in the illustrated embodiment, a track pin 110 may experience more a rapid increase in Delta-T than the wear failure sequence. Such a rapid increase may be indicative of a more abrupt failure event as opposed to gradual failure over time due to wear. As can be seen, the failure event sequence indicates a rapid rise in temperature from 10 F to 48 F over the span of one measurement timeframe. This rapid increase coupled with a temperature above 48 but less than 78 F may be indicative of early stage failure, whereas a temperature at or above 78 F may be considered late stage failure. For purposes of disclosure, the time of wear identifiers or time periods are depicted as sequential numbers—it should be understood that the amount of time between each measurement may vary from application to application, and may be static or variable during operation. Further, it should be understood that profiles for wear failure and failure events may vary depending on the application. For instance, the rapid increase profile associated with a failure event may be tailored to associate with more gradual increases in temperature or more rapid increases, depending on application. Likewise, the wear failure profile may be adapted to identify wear in a particular application.

In the illustrated embodiment of FIG. 10, the track pin sensor 300 may be configured to operate in conjunction with a conventional rubber stopper 120 for a conventional track pin 110. The track pin sensor 300 may be constructed to be physically similar to an oil plug that fits within the conventional rubber stopper, but with several structural and operational differences. For example, the track pin sensor 300 may include a shoulder cap 304 that may extend further from an exterior surface of the rubber stopper 120 than a conventional oil plug. On the other hand, the track pin sensor 300 may be similar to a conventional oil plug in that the track pin sensor 300 is configured to fit within an oil plug hole of the conventional rubber stopper 120 and enhance the seal between the rubber stopper 120 and the track pin 110. In this way, the track pin sensor 300 may be used to retrofit an existing track pin 110 and oil plug configuration. In the illustrated embodiment, the track pin sensor 300 may include a battery 310 as a power source, but it should be understood that the power source may be configured differently, and that for example the track pin sensor 300 may be self-powered according to any of the embodiments described herein.

The track pin sensor 300 may communicate information to a remote device 150 similar to the communication methodology described herein in connection with the track pin sensor 200.

II. Remote Device (e.g., a Hub Sensor)

Figure 3:
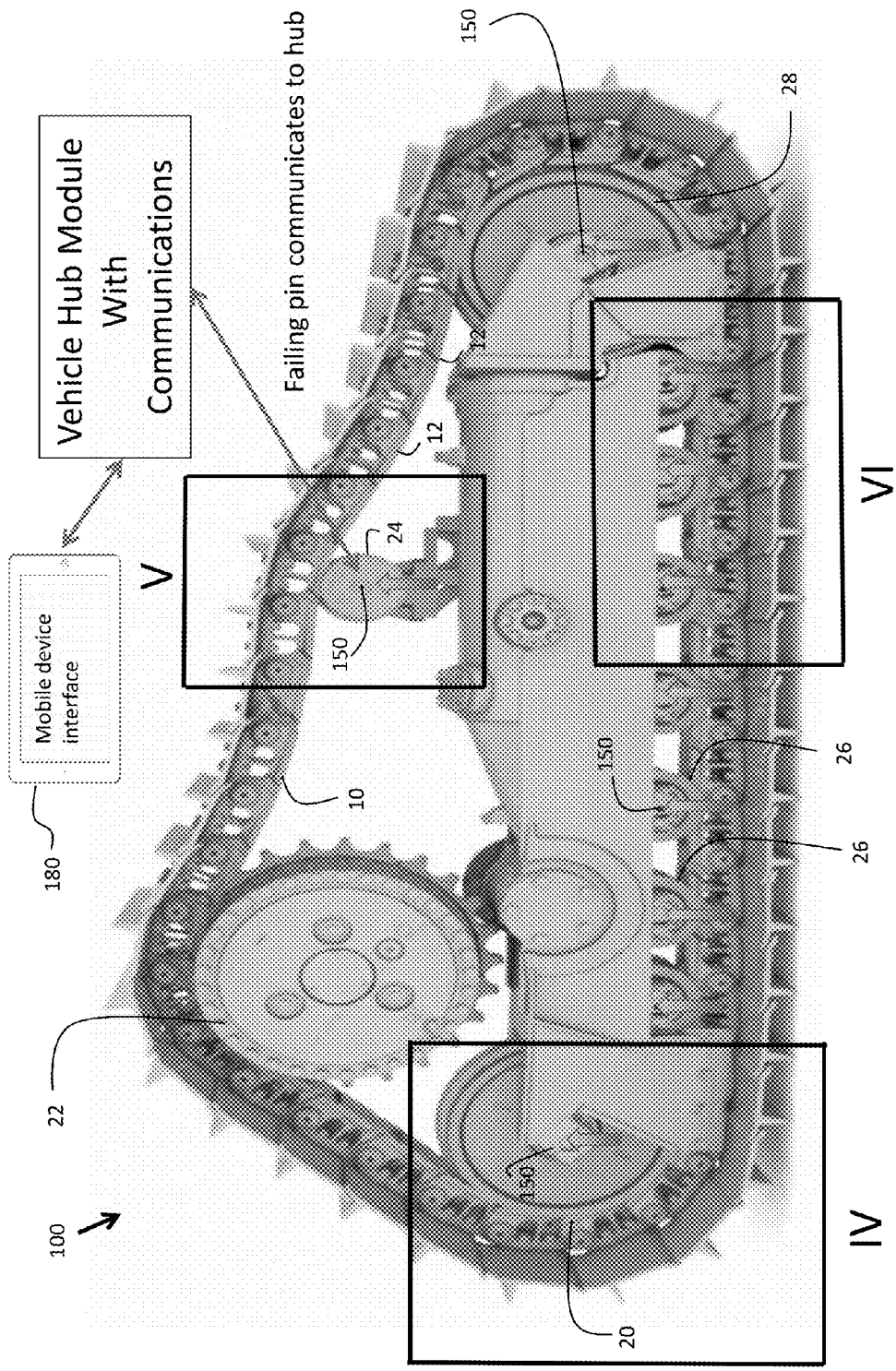
FIG. 3 shows possible locations for track chain sensors or nodes within the communication system as well as a remote device and a user device of the communication system, including a user device configured to facilitate identification and configuration of the track chain sensors.
Figure 4:
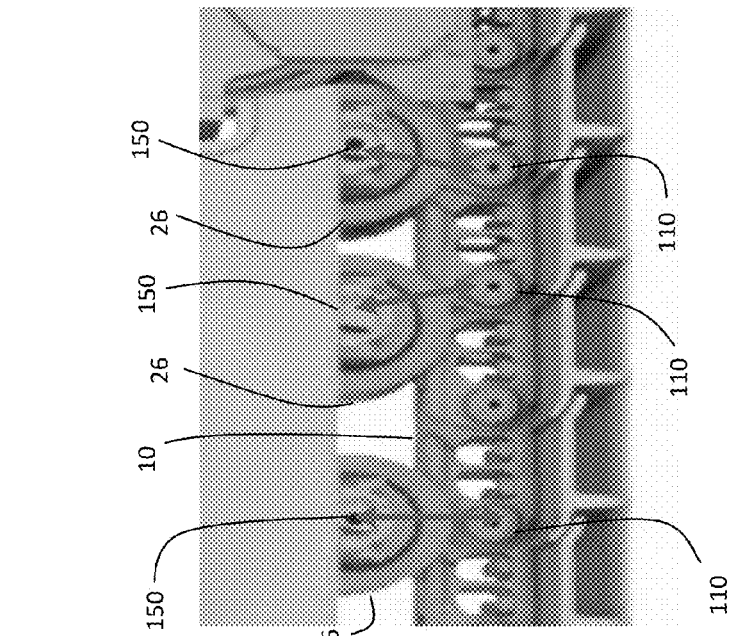
FIG. 4 shows an enlarged section of the communication system of FIG. 2.
Figure 5:
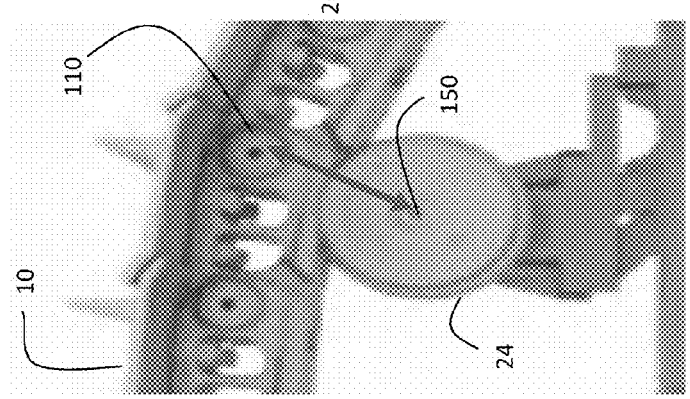
FIG. 5 shows an enlarged section of the communication system of FIG. 2.
Figure 6:
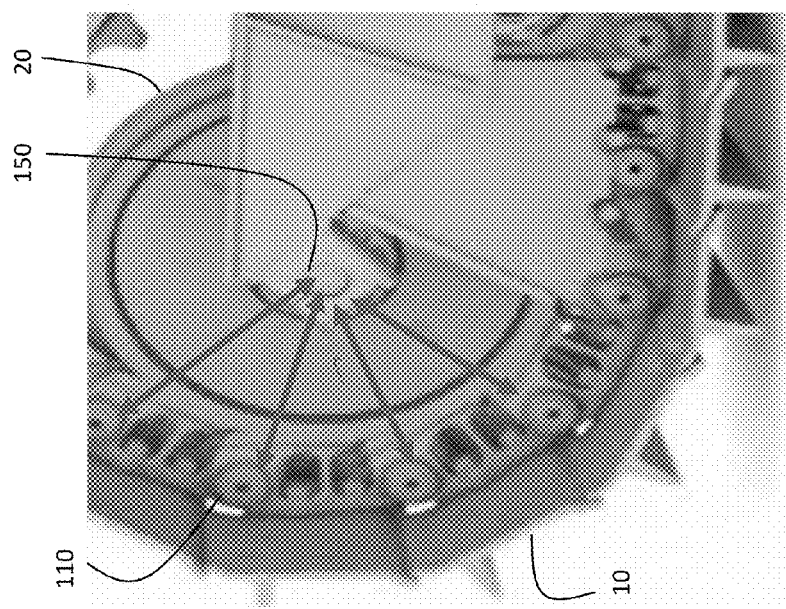
FIG. 6 shows an enlarged section of the communication system of FIG. 2.
Figure 7:
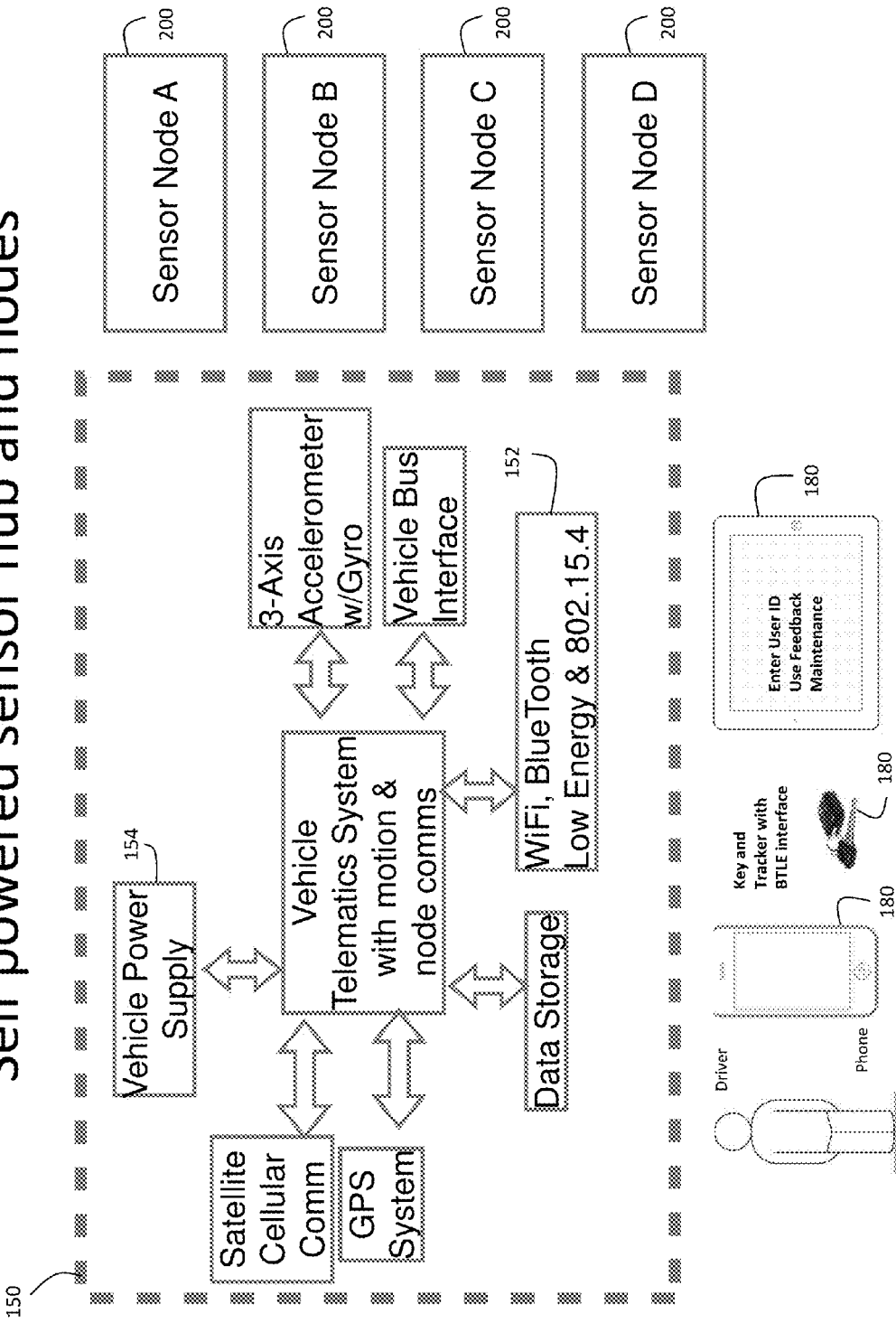
FIG. 7 shows a representative view of the communication system according to one embodiment, including a remote device and multiple sensor nodes.

A remote device according to one embodiment of the present disclosure is shown in FIG. 7 and generally designated 150. The remote device may be a configurable monitoring device located on heavy duty equipment. In one embodiment, the remote device may be a heavy duty interactive ("HDi") monitor, such as the HDi monitor described in International Patent Application No. PCT/US2016/013667 to Steketee et al., filed Jan. 15, 2016, entitled FLEET, EQUIPMENT AND MAINTENANCE INFORMATION MANAGEMENT SYSTEM, which is hereby incorporated by reference in its entirety. The terms HDi monitor, configurable monitor, and remote device can be used interchangeably. One embodiment of an HDi monitor 150 is illustrated in FIG. 7. This embodiment of an HDi monitor 150 includes a self-powered acceleration, location, driver ID, vehicle status and wear monitor. Other embodiments of HDi monitors may have different, additional, or less functionality. The HDi monitor may include a communication transceiver 152, such as a BlueTooth Low Energy (BTLE) transceiver configured to communicate with one or more track pin sensors 200. In one embodiment, based on a Received Signal Strength Indicator (RSSI) obtained from communicating with a plurality of track pin sensors 200, the HDi monitor 150 may be generally aware of which track pin sensors 200 are closer in proximity than others with respect to the HDi monitor 150.

An HDi system (or just HDi) according to one embodiment may include the communication system 100 and can refer to a suite of cost effective sensors to connect customers with their machines, work tools, and parts. That is, an HDi system may include machines/vehicles, work tools, parts, and a plurality of HDi monitors 150 that can be configured in a variety of different ways and may include a variety of different components. The HDi monitor 150 may be an add-on device installed to retrofit heavy equipment already in operation for several years. Additionally or alternatively, the HDi monitor may be incorporated into or integrated with the vehicle and computer systems. This type of integration may enable the HDI monitor 150 to utilize vehicle information, such as pressures, control status, engine sensors, and diagnostics, to enhance present performance and wear diagnostics.

In the embodiment depicted in FIG. 7, the HDi monitor 150 may include one or more of the following: a microprocessor monitoring system and signal processing system for recognizing patterns and activities, an RFID interface coupled to an RFID Tx/Rx coil, a GPS system, a cellular communication system, a wireless power charger, a battery and power supply, charging circuitry, a 3-axis accelerometer with a gyroscope, a vehicle bus interface, an ultrasonic transducer, and circuitry for communicating using WiFi, Bluetooth Low Energy & 802.15.4 protocols. Specifically, a low power BTLE transceiver 152 and potentially a longer distance transceiver may be included for communicating with a user device 180, if longer distance communications are desired.

In the illustrated embodiment, the self-powered hub or HDi monitor 150 may communicate status information or events, such as failures or abnormal operating conditions to a user device 180 based on information received from the one or more track pin sensors 200, 300, 400. Other types of information may be reported, as well or in the alternative, including, for example, acceleration information obtained in the HDi monitor 150. As depicted and described in connection with the illustrated embodiment of FIG. 3, a plurality of HDi monitors 150 may be disposed at various locations on a vehicle, including the hubs of the rollers that interface with the track chain 10.

The HDi monitor 150 may be directly powered by a vehicle power supply 154, or may be self-powered in a variety of ways, including, for example, a battery or a wireless power receiver.

In one embodiment, the monitoring device or HDi monitor 150 may be configured for operation or communication with the communication system 100, including one or more track pin sensors 200, 300, 400. Using a mobile device 180, a user may facilitate identification of where, on a representative, graphical track diagram, each track pin 110 is being utilized, thereby associating an identification code and associating the ID of each track pin sensor 200 to a physical location. The same mobile device 180 can communicate to the remote device 150 through BTLE. The thermoelectric device or sensor 200 can be triggered with a pin heater test device, resulting in activation of the sensor 200. This type of targeted test and response from individual sensors 20 may be used to generate the differential temperature that will power the alarm and indicate proper operation before installation. Further the test and response process may facilitate entry and physical location identification of each track pen sensor on the track chain 10. Proper operation of the sensor 200 may also be validated and confirmed through the mobile device 180 and set up application.

III. Method of Operation

Figure 13:
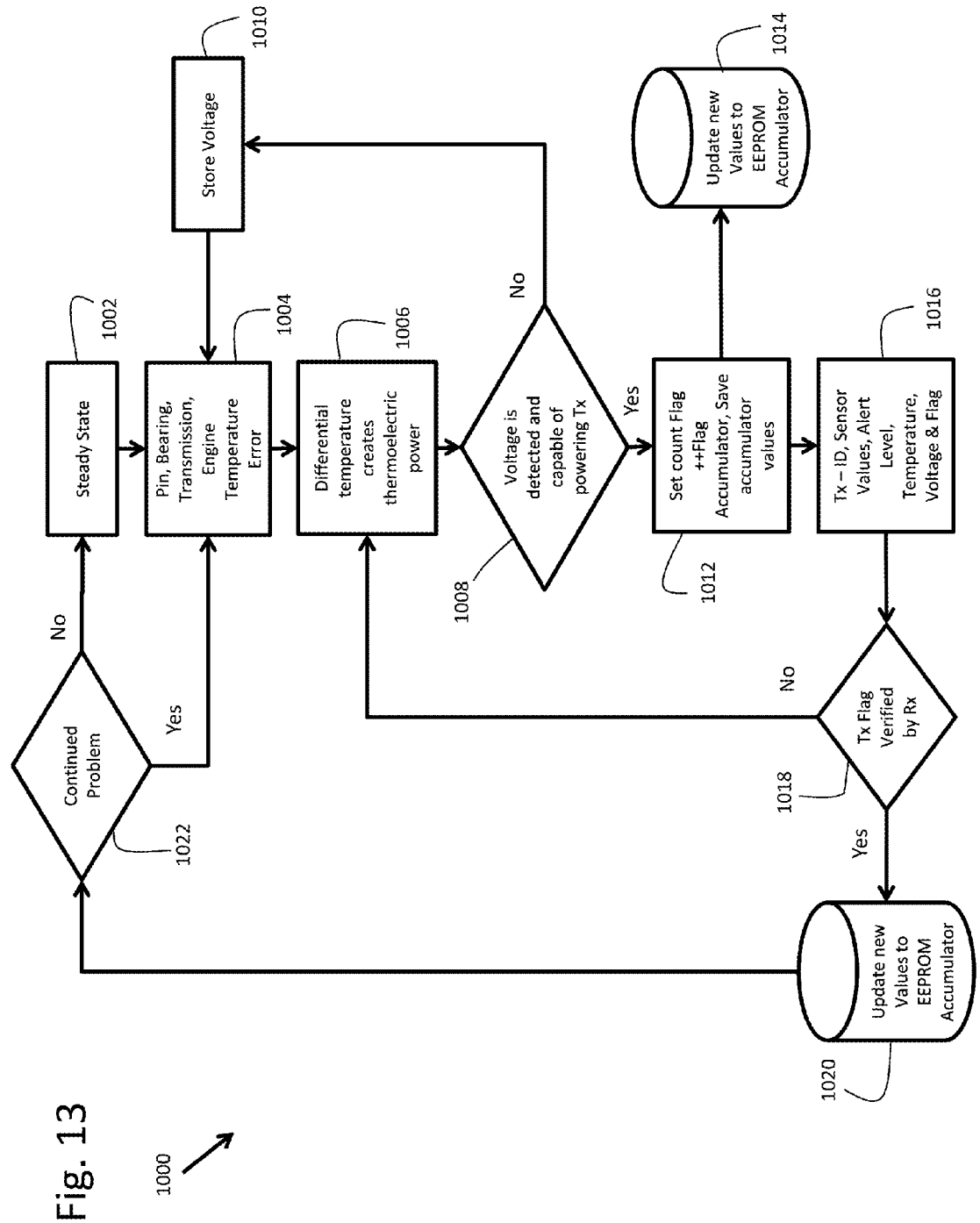
FIG. 13 shows a method of operation according to one embodiment.

A method of operation of a track pin sensor according to one embodiment is shown in FIG. 13 and generally designated 1000. The method may be implemented on one or more of the track pin sensors described herein, including the track pin sensors 200, 300, 400 described above. The method generally includes an operational loop, the steps of which are followed while power is available from the power supply (e.g., power is available from a thermoelectric generator). The operational loop may generally start at and return toward a steady state at which no errors or failure modes are detected or no power is available to operate. Step 1002. It should be understood that one or more of the track pin sensors 200, 300, 400 may be configured to be powered during normal operation or in absence of a failure mode, and that during such normal operation, the track pin sensor 200, 300, 400 may remain in the steady state mode.

If an error or failure mode is detected, such as a pin, bearing, transmission or engine temperature exceeding a threshold, as described herein, the failure mode itself may generate energy in the thermoelectric generator. Step 1004. This energy may power the device, or may be accumulated until enough energy has been stored to power the device and communicate information wirelessly. Steps 1008, 1010. With sufficient energy available to communicate information and power the sensor, a controller of the sensor may retrieve a value or flag associated with an error accumulator from memory, increase the value, and store the increased value in memory. Steps 1012, 1014. Additionally or alternatively, sensor readings or status information, or both, may also be stored in memory. Using nonvolatile memory enables the sensor to track error or failure mode events even in cases where there is insufficient power to keep the sensor active. As an example, if the sensor is experiencing fluctuating readings, such as a failure mode being detected and then not detected, and the sensor becomes powered and unpowered as a result, the sensor may track the accumulation of failure mode events to communicate this information the remote device 150.

The sensor may wirelessly communicate information relating to the failure mode, including, for example, identification information about the sensor (e.g., to identify the specific track pin experiencing a failure mode), sensor values, alert levels, temperature, voltage and the accumulator value or flag, or a combination thereof. Step 1016. The sensor may wait for a period of time to receive an acknowledgement of the transmission. Step 1018. If no acknowledgement receipt is received within the wait period, the sensor may reiterate the loop of accumulating power and transmitting information relating to a failure mode. Steps 1018, 1006. If an acknowledgement receipt is received, the sensor may store one or more values or sensor readings in memory similar to Step 1014, and return toward steady state if the failure mode is no longer present. Step 1022, 1002 If the failure mode remains present, the sensor may reiterate the loop and transmit further information about the failure mode. Steps 1022, 1004.

It should be noted that the thermoelectric power generated from a system according to one embodiment may be used for other sensors and measurement systems. An example of another sensor system includes detecting a range or distance between pins. For instance, an ultra-wide band (UWB) radio transceiver may be incorporated into the track pin sensor, or disposed on or in proximity to the track pin, to measure the distance between track pins 110 or the distance from one or more track pins 110 to a remote device 150, or a combination thereof. An example of such a UWB transceiver is sold by DecaWave under the part name DWM1000, and is capable of locating of objects in real time while also enabling communication of information as described herein. The measured distance or distances may be tracked, and optionally averaged over time. The tracked distance between pins 110 or the tracked distance from the pins to a remote device 150, or both, may be used as a basis for determining wear over time. Another example sensor system may include one or more accelerometers disposed to sense acceleration in one or more axes. Data from an accelerometer may be indicative of and used as a basis for determining when abnormal operation is starting to develop or when abnormal operation is present, or both.

In one embodiment of the present disclosure, the use of insulation and the environmental coating with respect to the track pin sensor 200, 300, 400 may facilitate existence of a differential temperature for some period of time. This time may be long enough to provide power to report an error condition or failure mode, and to confirm receipt of that information from the hub or remote device 150. The illustrated embodiment of FIG. 13 depicts one or more steps focused on a logical sequence to confirm and log the number of times that error or failure mode has occurred with respect to a particular sensor and sensor ID. The method according to FIG. 13 may also include recording a level of temperature and voltage sensor signals over time to enable a determination of whether a condition is becoming worse over time. This type of tracking may allow the hub or remote device 150 to share data to a cloud device or user device 180 for further analysis and analytics. The thresholds, limits and sensor information obtained by the track pin sensor can then be analyzed to generate additional profiles of operation, including new thresholds that facilitate identification of pre failure, mid failure and eminent failure.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The invention claimed is:

1. A communication system for monitoring operational status of a track chain for heavy equipment, said communication system comprising:
    a track pin configured to facilitate interconnections between track sections of the track chain, wherein said track pin includes an internal void;
    a track pin sensor disposed at least partially within said internal void of said track pin, said track pin sensor including:
        a temperature sensing element configured to provide an output indicative of a temperature characteristic of said track pin;
        a wireless transmitter configured to communicate information to a remote device, said information being indicative of an operational state of said track pin; and
        a controller operably coupled to said temperature sensing element and said wireless transmitter, said control configured to determine said information based on said output of said temperature sensing element.

2. The communication system of claim 1 wherein said temperature sensing element is a thermoelectric generator configured to supply power to said wireless transmitter and said controller to facilitate communication of said information, and wherein a voltage output of said thermoelectric generator is indicative of a temperature characteristic of said track pin.

3. The communication system of claim 2 wherein said track pin sensor remains dormant until after occurrence of a failure condition.

4. The communication system of claim 3 wherein said failure condition includes generation of heat, and wherein said thermoelectric generator is configured to provide power said wireless transmitter and said controller based on said heat generation.

5. The communication system of claim 1 wherein said remote device is disposed on or in proximity to a rotating hub of one or more lower rollers of a heavy vehicle track drive system, and wherein said track pin sensor is configured to communicate wirelessly with said remote device.

6. The communication system of claim 1 further comprising a user device configured to communicate with at least one of said track pin sensor and said remote device, said user device configured to monitor status of the track pin sensor.

7. The communication system of claim 6 wherein said user device is configured to aid initializing a setup of a plurality of track pin sensors for a plurality of respective track sections, wherein said user device is configured to map a physical location of said plurality of track pin sensors on said track chain.

8. The communication system of claim 7 wherein each of track pin sensors is configured to activate to communicate via said communication system in response to contact with a test probe, and wherein said user device enables identification of the physical location based on activation of a track pin sensor by the test probe.

9. The communication system of claim 1 wherein said information communicated by said track pin sensor includes at least one of an identification code of said track pin sensor, one or more alert levels, a temperature, a voltage and a operation event accumulator value.

10. A track pin sensor for monitoring an operational status of a track pin of a track chain for heavy equipment, said track pin sensor comprising:
a temperature sensing element configured to provide an output indicative of a temperature characteristic of said track pin;
a wireless transmitter configured to communicate information to a remote device, said information being indicative of an operational state of said track pin, wherein said remote device is disposed on or in proximity to a rotating hub of one or more lower rollers of a heavy vehicle track drive system, and wherein said track pin sensor is configured to communicate wirelessly with the remote device; and
a controller operably coupled to said temperature sensing element and said wireless transmitter, said control configured to determine said information based on said output of said temperature sensing element.

11. The track pin sensor of claim 10 wherein said temperature sensing element is a thermoelectric generator configured to supply power to said wireless transmitter and said controller to facilitate communication of said information, and wherein a voltage output of said thermoelectric generator is indicative of a temperature characteristic of said track pin.

12. The track pin sensor of claim 11 wherein said track pin sensor remains dormant until after occurrence of a failure condition.

13. The track pin sensor of claim 12 wherein said failure condition includes generation of heat, and wherein said thermoelectric generator is configured to provide power said wireless transmitter and said controller based on said heat generation.

14. The track pin sensor of claim 10 wherein said track pin sensor is configured to communicate with a user device to transmit status information to the user device.

15. The track pin sensor of claim 10 wherein said information communicated by said track pin sensor includes at least one of an identification code of said track pin sensor, one or more values, one or more alert levels, a temperature, a voltage and a operation event accumulator value.

* * * * *